United States Patent
Besemer et al.

(10) Patent No.: US 6,916,466 B2
(45) Date of Patent: Jul. 12, 2005

(54) COUPLING OF MODIFIED CYCLODEXTRINS TO FIBERS

(75) Inventors: Arie Cornelis Besemer, Amerongen (NL); Anne Mieke Yvonne Wilhelmina Verwilligen, Zeist (NL); Harm Jan Thiewes, Woudenberg (NL)

(73) Assignee: SCA Hygiene Products AB, Gothenburg (SE)

( * ) Notice: Subject to any disclaimer, the term of this patent is extended or adjusted under 35 U.S.C. 154(b) by 151 days.

(21) Appl. No.: 10/192,715

(22) Filed: Jul. 11, 2002

(65) Prior Publication Data

US 2003/0026828 A1 Feb. 6, 2003

Related U.S. Application Data

(60) Provisional application No. 60/304,111, filed on Jul. 11, 2001.

(51) Int. Cl.[7] .......................... A61K 7/035; A61K 9/00; A61K 9/70; A01N 25/24; A01N 25/34
(52) U.S. Cl. ..................... 424/69; 424/400; 424/402; 424/407; 424/443; 424/444; 604/356
(58) Field of Search .................. 424/69, 400, 402, 424/407, 412, 413; 604/356

(56) References Cited

U.S. PATENT DOCUMENTS 5,429,628 A * 7/1995 Trinh et al. ................ 604/359

FOREIGN PATENT DOCUMENTS

| JP | 64-15049 | 1/1989 | |
|----|----------|--------|---|
| WO | WO 94/22501 | 10/1994 | |
| WO | WO 95/07303 | 3/1995 | |
| WO | WO 9507303 A1 * | 3/1995 | ........... C08B/37/00 |
| WO | WO 99/06078 | 2/1999 | |
| WO | WO 99/57158 | 11/1999 | |
| WO | WO 00/26257 | 5/2000 | |
| WO | WO 00/50388 | 8/2000 | |
| WO | WO 00/50621 | 8/2000 | |
| WO | WO 0066187 A1 * | 11/2000 | |
| WO | WO 00/66187 | 11/2000 | |
| WO | WO 01/48025 | 7/2001 | |
| WO | WO 0148025 A1 * | 7/2001 | |

OTHER PUBLICATIONS

Denter et al. "Surface Modification of Synthetic and Natural Fibres by Fixation of Cyclodextrin Derivatives", Journal of Inclusion Phenomena and Molecular Recognition in Chemistry, vol. 25: 197–202, 1996.*

Patent Abstracts of Japan, vol. 2000, No. 01, Jan. 31, 2000, JP 11 279206 (SNC: KK: Sakairi Nobuo), Oct. 12, 1999.

Denter, U., et al., "Verfahrenstechnische Methoden zur permanenten Fixierung von Cyclodextrinderivaten auf textilen Oberflaechen," Textilveredlung, vol. 32, No. 1/2, 1997, pp. 33–39.

Denter, U., et al., "Surface Modification of Synthetic and Natural Fibres by Fixation of Cyclodextrin Derivatives," Journal of Inclusion Phenomena and Molecular Recognition in Chemistriy, vol. 25, 1996, pp. 197–202.

* cited by examiner

Primary Examiner—Gollamudi S. Kishore
Assistant Examiner—S. Tran
(74) Attorney, Agent, or Firm—Burns, Doane, Swecker & Mathis, L.L.P.

(57) ABSTRACT

Cyclodextrins and other ecapsulating oligosaccharides can be bound to fibrous and/or polysaccharidic carriers by ionic bonds. The ionic bonds can be produced by introducing cationic or anionic groups into the cyclodextrins, and where appropriate, by introducing oppositely charged groups in the carrier material. The products can be used for odor control in the fibrous material.

10 Claims, No Drawings

COUPLING OF MODIFIED CYCLODEXTRINS TO FIBERS

This application claims priority under 35 U.S.C. § 119 to U.S. Provisional Application No. 60/304,111 entitled COUPLING OF MODIFIED CYCLODEXTRINS TO FIBERS and filed on Jul. 11, 2001, the entire content of which is hereby incorporated by reference.

FIELD OF THE INVENTION

The invention relates to odour regulation in tissue and hygiene products using modified compounds capable of absorbing odorous components from liquids and of releasing odour-regulating compounds.

BACKGROUND OF THE INVENTION

It is known from JP-A-1-015049 to add cyclodextrins to paper diapers for the purpose of deodorizing the paper diaper. A fragrance is included in the cyclodextrin and can be released in the diaper, while absorption of malodours by the non-included cyclodextrin adds to the deodorizixg effect. Similarly, WO 94/22501 describes articles containing cyclodextrin having a particle size below 12 μm, especially below 5 μm, for removal of odour from diapers and paper towels. On the other hand, cyclodextrin particles of greater than 12 μm, typically around 100 μm, are said to be effective for odour control in absorbent articles according to WO 99/06078. WO 00/66187 discloses odour-controlled superabsorbent polymers containing cyclodextrins or cyclodextrin ethers such a methyl- or hydroxyalkyl-cyclodextrins homogeneously distributed therein.

WO 01/48025 discloses the incorporation of non-derivatized cyclodextrin onto cellulose fibres by covalent bonding of the cyclodextrin using a polymeric anionic reagent such as polymaleic acid or by binding the cyclodextrin to dialdehyde groups on the cellulose.

While cyclodextrins have been known for a long time as being useful for inclusion of a variety of agents, including odour-regulating agents, the most important member thereof, β-cyclodextrin, has a poor solubility and hence a difficult applicability in various product types, such as hygiene products.

SUMMARY OF THE INVENTION

It was found according to the invention, that the utility of cyclodextrins for absorbing various compounds from liquids into solid supports, especially paper and other cellulosic and/or fibrous carriers, can be improved by coupling the cyclodextrins to the solid support. It was also found that, e.g. in hygiene products for use in contact with the human skin, the immobilisation of the cyclodextrins avoids their migration to the skin or, in other uses, to other materials. The coupling can be performed either by ionic interaction, which was found to be easily realized, or by specific covalent bonding.

DESCRIPTION OF THE INVENTION

The carrier: The carrier to which cyclodextrin and other encapsulating agents with or without inclusion compounds can be coupled has a fibrous structure and is substantially water-insoluble. It is usually a polymer having a partial or full polysaccharide nature, such as in cellulose, hemicellulose or synthetic carbohydrates. The molecular weight of the carrier is preferably above 5 kDa; more preferably from 100 kDa to 10 MDa. Lower molecular weights are also feasible, as long as the polysaccharide is water-insoluble. The polymer may be natural or synthetic, and may be a mixture of various polymer types, such as cellulose-acrylate, or starch-acrylate, or starch-protein and the like. The fibrous structure is preferably part of an absorbent product, for use in absorbing fluids such as washing fluids, body fluids and the like. Examples include paper and paper products, tissues and the like, especially for use in hygiene products, such as such as kitchen rolls, facial tissues, bathroom towels, sanitary napkins and diapers.

The encapsulating agent: These are products that are capable of complexing or encapsulating molecules of interest, such as biologically active agents (drugs, biocides, attractants, repellants, diagnostic agents, regulators, etc,), odours, fragrances, and the like, for the purpose of absorption or slow release. These primarily include cyclodextrins, i.e, cyclooligomers of anhydroglucose units (AGU), having at least 6 AGU (α-cyclodextrin), preferably 7 AGU (β-cyclodextrin), possibly 8 (γ-cyclodextrin) or more AGU (δ- and higher cyclodextrins). Furthermore, acyclic analogues having complexing and/or encapsulating capacities, such as helical oligoglucoses (α-1,4: dextrins, or β-1,3) can also be coupled and used according to the invention. The encapsulating agents, especially cyclodextrins, are used in ionic form.

In this context, oligo- means having up to 20 recurrent units. The cyclodextrins and analogues may be unmodified or modified, e.g. by acylation, alkylation, hydroxyalkylation, etc., apart from any modification that would be necessary in the coupling process, as detailed below. The encapsulating agents are referred to below as cyclodextrins (CD) for the sake of simplicity, but it should understood that the analogous agents as described here are always covered as well, unless they are explicitly excluded.

Ionic coupling: Ionic coupling of CD to fibrous carriers can be effected by applying an electronic charge on the carrier and by applying the opposite charge to the CD. For example, the carrier can be negatively charged (anionic derivatisation) by carboxyalkylation, sulphonation, phosphorylation and the like, using chloroacetic acid, chloroethanesulphonic acid or vinyl sulphonic acid, phosphoric acid or its chloride, and the like, respectively. A mixed anionic derivatisation can be achieved e.g by addition of maleic anhydride, followed by addition of bisulphite, resulting in anionic groups of the type: —O—CO—CH—CH($SO_3$H)—COOH (or its deprotonated forms). Alternatively, anionic derivatisation can be achieved by oxidizing the carrier carbohydrate to a slight extent. The CD can then be made cationic as described in more detail below, and then be combined with the anionic carrier.

Alternatively, and more preferably, the carrier can be positively charged (cationic derivatisation) by amino- or azido-alkylation, or oxidation to introduce aldehyde functions followed by reaction with amines (reductive amination) or other nitrogen-containing reagenats. Cationisation of the carrier can also be achieved by applying a cationic additive such as PAE (poly(amide)amine-epichlorohydrin) to the carrier. The anionic or cationic derivatisation is performed to an extent that allows sufficient coupling of oppositely charged, and depending on the particular use of the coupling product. In general, a degree of ionisation of 0.1–50 ionic charges per 100 monomer units of the carrier, preferably from 1 to 20 charges per 100 units.

Cationic charges can be introduced into CD molecules in a manner known per se. Suitable methods include reaction of CD with chloroethyl-trimethylammonium chloride or glycidyl trimethylammonium chloride or similar reagents, resulting in quaternary ammoniumalkyl derivatives. These have a full positive charge irrespective of the pH of the system in which the coupling products ions incorporated. Alternatively, the lower substituted aminoalkyl derivative can be prepared, which are suitable for use in neutral and acidic conditions. Amine or ammonia groups can also be introduced into CD by first introducing aldehyde functions, either by periodate oxidation, or by TEMPO-mediated oxidation using hypochlorite or a peracid, as described e.g. in WO 95/07303, WO 99/57158, WO 00/50388 and WO 00/50621, followed by reaction with an amine, preferably under reducing conditions. One cationic charge per CD molecule is generally sufficient for coupling. Preferably the CD will have a DS (degree of substitution) for cationic groups between 0.1 and 0.3, most preferably 0.17–0.25 for α-cyclodextrins, 0.14–0.22 for β-cyclodextrins, and 0.12–0.2 for γ- and higher cyclodextrins.

Anionic charges can be also introduced onto CD molecules in a manner known per se. Suitable methods therefore include oxidation of CD with e.g. periodate, followed by chlorite, or by direct oxidation with hypochlorite, resulting in one or more glucose units being opened to dicarboxyoxabutylene [—O—CH(COOH)—CH(CH$_2$OH)—O—CH(COOH)—] units, or with periodate, followed by oxidation with peracetic acid and bromine, as described in WO 00/26257, resulting in similar ring-opened units with both aldehyde and carboxyl groups. Anionic derivatisation of CD can also be effected by carboxyalkylation, sulphonation, phosphorylation and the like, as explained above for anionisation of the carrier. A further anionic CD derivative is a hydroxytriazinyl derivative, obtainable by reaction of CD with trichloro-s-triazine.

Preferably however, the oxidation is focussed on the 6-hydroxymethyl groups, using hypochlorite or persulphuric acid and nitroxyl-mediation, e.g. using TEMPO or 4-acetamido-TEMPO, as mentioned above. Again, the resulting DS for anionic charges in preferably between 0.1 and 0.3, more preferably 0.17–0.25 for α-cyclodextrins, 0.14–0.22 for β-cyclodextrins, and 0.12–0.2 for γ- and higher cyclodextrins.

Another method for coupling involves derivatisation of the CD with a group that will smoothly react with hydroxyl functions of the carrier. A suitable example of such derivatisation is reaction with a halotriazine.

Utility: The products of the invention are especially useful as an odour regulator in hygiene products, such as diapers, napkins and tissue products such as wipes for kitchen rolls and facial tissues, bathroom towels etc., by scavenging malodours. They can also assist in suppressing bacterial growth, resulting in reduced ammonia production e.g. in diapers and panty liners. The amount of complexing or encapsulating oligosaccharide on the fibrous carrier can be an amount varying between 1 and 300 mg/g, preferably between 1 and 200 mg/g and most preferably between 1 and 100 mg/g. The odour regulation can be effected in two ways. Firstly, the oxidized cyclodextrins serve to absorb odorous components from the fluid or solid material for which the hygiene material is used, such as sulphur compounds, amines, aromatic compounds, carbonyl compounds and the like. Secondly, a desired neutralizing odour or fragrance may be incorporated in the product prior to its use, and can be released or exchanged in use, resulting in a neutral and/or, pleasant odour in the product in use. Examples of suitable fragrances include terpenoid compounds such as linalool, menthone, menthol, limonene and pinene.

Other applications are in the pharmaceutical and medical field, or in biocides, for odour control, stabilisation of encapsulated compounds to light, oxidation and vaporisation, slow release, and in enantiomer separation.

EXAMPLE 1

Ionic Binding

Coupling of 6-carboxy β-cyclodextrin to Cationic Fibres

6-Carboxy β-cyclodextrin was prepared by oxidation of β-cyclodextrin with 4-acetamido-TEMPO and hypochlorite. Thus, 7.64 g β-cyclodextrin, 150 mg NaBr and 150 mg 4-acetamido TEMPO were added to 300 ml water. Sodium hypochlorite was added in doses of 0.20 ml. During reaction the pH was kept at 9.3 by addition of NaOH controlled by a pH stat. After each dose the reaction was allowed to proceed until no further NaOH consumption was seen. Two samples were prepared with a degree of oxidation (DO) of 0.11 and 0.38, respectively.

Cationic fibres were prepared by oxidation of sulphate pulp fibres (SCA Östrand mill) with sodium periodate (DO= 10% dialdehyde) and the obtained aldehyde groups were subsequently reacted with Girard's reagent T (acethydrazide trimethylammonium chloride). Hereby fibres containing 10% cationic groups were obtained.

Next 30 mg of 6-carboxy β-cyclodextrin (acidic form) was dissolved in 5 ml de-mineralized water and added to 1 g (dry weight) of cationic fibres containing ca, 60% water. The fibres were incubated at 120° C. for about 1 hour. Afterwards the sample was washed with 200 ml de-mineralized water to remove non-bound oxidized cyclodextrin and dried in a fluidized bed dryer for 30 minutes at 60° C. (Samples I and II).

EXAMPLE 2

Ionic Binding

Coupling of Carboxymethylated β-cyclodextrin to Cationic Fibres

Carboxymethylated β-cyclodextrin was prepared by reaction with monochloroacetic acid at pH 12. The product obtained had a degree of substitution of 0.36. The cationic fibres were prepared as described in Example 1.

30 mg of carboxymethyl β-cyclodextrins were adsorbed on 1 g cationic fibres (dry weight), and washed with water and dried, as described in Example 1 (Sample III).

EXAMPLE 3

Ionic Binding

Coupling of Monochlorotriazinyl β-cyclodextrin to Cationic Fibres

Cationic fibres were prepared by adding 5 g fibres to a solution containing 0.5 g PAE (poly(amide)amine-epichlorohydrin). This mixture was incubated overnight at room temperature. Next excess liquid was removed and the fibres were dried at 120° C. Finally, non-bound PAE was removed by washing the fibres.

Then, 30 mg monochlorotriazinyl β-cyclodextrin ((MCT-CD) obtained from Wacker Chemie) was dissolved in 20 ml demineralized water and added to 1 g (dry weight) cationic fibres. This mixture was allowed to stand at room temperature for 20 minutes, resulting in ionic bonding (Sample IV). Non-bound MCT-CD was removed by washing the fibres with de-mineralized water. Next the fibres were dried for 10 minutes at 80° C. in a fluidized bed dryer, which does not result in covalent coupling. As covalent coupling requires temperatures in the order of 140–175° C. (as described by Reuscher and Hirsenkorn in *Journal of Inclusion Phenomena and Molecular Recognition in Chemistry*, 25 (1996) p.

195), it is assumed that at these mild conditions of drying, 10 minutes at 80° C., no chemical reaction between the fibres and MCT-CD occurs.

EXAMPLE 4

Covalent Bonding

Coupling of Carboxymethyl-β-cyclodextrin to Pulp Fibres

Carboxymethyl β-cyclodextrin, prepared as described above, was (250 mg) was reacted with wet 1.66 g pulp fibres (dry weight 1 g) for 1.5 hours at 150° C. After reaction the fibres were washed with water to remove non-reacted carboxymethyl β-cyclodextrin (sample V).

EXAMPLE 5

Covalent Bonding

Coupling of Monochlorotriazinyl-β-cyclodextrin to Pulp Fibres 30 mg monochlorotriazinyl β-cyclodextrin (obtained from Wacker Chemie) was dissolved in 5 ml 250 mM $Na_2CO_3$ pH 11 and added to 1 g (dry weight) sulphate pulp fibres containing about 60% water. The sample was incubated at 120° C. for about 1 hour and afterwards suspended in 200 ml demineralized water to remove non-reacted cyclodextrin. Finally, the fibres were dried in a fluidized bed dryer for 30 minutes at 60° C. (sample VI).

EXAMPLE 6

Measuring Binding Capacity of Cyclodextrinated Fibres

The binding capacity of the modified fibres was determined colorimetrically, 2 ml of 20 mg/l phenolphthalein solution in 100 mM $Na_2CO_3$ buffer pH 10.3 was added to 1 g of dry modified fibres. Next the liquid was squeezed out of the fibres and absorption of the solution was measured at 554 nm. The results are summarized in Table 1. The lower the absorption in the squeezed solution, the more phenolphthalein has been encapsulated by the cyclodextrinated fibres. Table 1 shows that the difference in absorption between the samples and their blanks is considerably bigger when ionically bound CD, carboxymethyl CD (Sample III) and MCT-CD (Sample IV), is compared to covalent bound CD, (Sample V and VI).

TABLE 1

Phenolphthalein binding ability of fibres treated with cyclodextrin derivatives

| Sample | Description | Absorption at 554 nm |
|---|---|---|
| | starting solution | 1.580 |
| | catiopic (Girard reagent T) fibres (blank) | 0.484 |
| I | ionically bound 6-carboxy β-cyclodextrin, DO 0.11 | 0.343 |
| II | ionically bound 6-carboxy β-cyclodextrin, DO 0.38 | 0.314 |
| III | ionically bound 6-carboxymethyl β-cyclodextrin, DS 0.36 | 0.146 |
| | cationic (PAE) fibres (blank) | 1.120 |
| IV | ionically bound MCT-CD-β-cyclodextrin | 0.076 |
| | pulp fibres (blank) | 0.678 |
| V | covalently bound carboxymethyl β-cyclodextrin | 0.454 |
| VI | covalently bound monochlorotriazinyl β-cyclodextrin | 0.063 |

EXAMPLE 7

Absorption Test with Ionically Bound MCT-CD Tissues

The ability of a cyclodextrin-containing tissue to remove a hydrophobic agent was shown visually by spreading an amount of phenolphthalein on a smooth surface, and attempting to remove the phenolphthalein using untreated tissue and tissue containing monochlorotriazinyl β-cyclodextrins (MCT-CD).

For each test a smooth surface (10 cm×10 cm) was polluted by spreading a phenolphthalein solution (20 μmol phenolphthalein) in ethanol on it. Next the ethanol was evaporated, and thus a layer of dry phenolphthalein was obtained.

A cyclodextrin-containing tissue (11×11 cm) was prepared by adding an MCT-CD solution in water (containing approximately 100 μmol MCT-CD) to a tissue that has cationic charge (treated with excess PAE) and next drying it in a fluidized bed dryer at 80° C. for 15 minutes. Before wiping the surface, each tissue was wetted with 5 ml of 1 M $Na_2CO_3$ buffer, pH 10.3 (convert phenolphthalein to its pink form). Next the surfaces were wiped until as much of the phenolphthalein as possible was removed. After wiping, the untreated tissue had completely turned dark pink, and it appeared that is was not possible to completely clean the surface, since the tissue was releasing excess of phenolphthalein. However, the surface cleaned by the MCT-CD containing tissue was completely clean, and the tissue showed some light pink spots, but was overall white.

We claim:

1. A process for coupling a cyclic oligosaccharide to a polysaccharidic carrier comprising negatively charging the carrier by carboxyalkylation, sulphonation, oxidation or phosphorylation; positively charging the oligosaccharide; and coupling the cyclic oligosaccharide to the carrier;

wherein the cyclic oligosaccharide is a cyclodextrin.

2. A process for coupling a cyclic oligosaccharide to a polysaccharidic carrier comprising positively charging the carrier by amino-alkylation, azido-alkylation, oxidation, or applying a cationic additive to the carrier; negatively charging the oligosaccharide; and coupling the cyclic oligosaccharide to the carrier;

wherein the cyclic oligosaccharide is a cyclodextrin, wherein the cationic additive is poly(amide)amine-epichlorohydrin.

3. An absorbent hygiene product comprising a coupling product of a derivative of a cyclic oligosaccharide containing at least 1 ionic group per molecule to a polysaccharidic carrier coupled according to the process of claims 1 or 2 containing 0.1–50 ionic groups per 100 monomer units of the polysaccharide, the charges of the ionic groups of the oligosaccharide and of the polysaccharidic carrier being opposite.

4. A hygiene product according to claim 3, wherein the cyclic oligosaccharide is a cyclodextrin or a cyclodextrin derivative.

5. A hygiene product according to claim 3, wherein the carrier is a cellulosic fiber.

6. A hygiene product according to claim 3, wherein the carrier is an anionic carrier having a degree of substitution of between 0.001 and 0.2 and the cyclic oligosaccharide is a cationic oligosaccharide containing at least one amine or ammonium group per molecule.

7. A hygiene product according to claim 3, wherein the carrier is a cationic carrier having a degree of substitution of between 0.001 and 0.1 and the cyclic oligosaccharide is an oxidized or carboxymethylated oligosaccharide having a degree of carboxyl substitution of at least 0.14.

8. An absorbent hygiene product comprising a coupling product of a chloro-hydroxytriazine derivative of a cyclic oligosaccharide coupled according to the process of claims 1 or 2 containing at least 1 ionic group per molecule and a cellulosic carrier

9. A process of controlling odor from liquids comprising contacting the liquid with a coupling product obtained by the process of claim 1.

10. A process of controlling odor from liquids comprising contacting the liquid with a coupling product obtained by the process of claim 2.

* * * * *